United States Patent [19]

Mochizuki

[11] Patent Number: 5,370,782

[45] Date of Patent: Dec. 6, 1994

[54] ELECTROPHORETIC APPARATUS

[75] Inventor: Takanori Mochizuki, Kyoto, Japan

[73] Assignee: Shimadzu Corporation, Kyoto, Japan

[21] Appl. No.: 66,244

[22] Filed: May 25, 1993

[30] Foreign Application Priority Data

May 29, 1992 [JP] Japan .................. 4-138568

[51] Int. Cl.$^5$ ............................................. B01D 61/46
[52] U.S. Cl. ................................................. 204/299 R
[58] Field of Search ........................ 204/299 R, 182.8

[56] References Cited

PUBLICATIONS

Toneguzzo et al., A System for On-Line Detection and Resolution of Radiolabeled DNA Molecules and its Application to Automated DNA Sequence Analysis, Biotechniques, 7(8), 1989.

Voet and Voet, Biochemistry, pp. 830–835, 1990.

Primary Examiner—John Niebling
Assistant Examiner—Edna Wong
Attorney, Agent, or Firm—Nikaido, Marmelstein, Murray & Oram

[57] ABSTRACT

An electophoretic apparatus for determining the base sequence of DNA has a device for introducing a sample, a device for controlling the temperature of the sample in the sample introducing device, a device for causing electrophoresis of the temperature-controlled sample in a gel to separate it into fragments, and a device for analyzing those fragments. The apparatus makes it possible to carry out successively and automatically a process which determines the base sequence of DNA by treating DNA in accordance with the Sanger method to form complementary DNA fragments of different lengths ending specifically with four different kinds of bases, separating those fragments from one another electrophoretically, and identifying the base at the end of each of those fragments.

14 Claims, 2 Drawing Sheets

5,370,782

ELECTROPHORETIC APPARATUS

BACKGROUND OF THE INVENTION

This invention relates to an electrophoretic apparatus, particularly one which employs a gel as a medium.

There is known an electrophoretic process which employs a slab or capillary gel for determining the sequence of bases in DNA. The sequence of bases in DNA is determined by the Sanger method which employs an M13 vector, or plamsmid PUC. The Sanger method which employs plasmid PUC, however, often makes it difficult to decode the sequence of bases in DNA correctly because of the stacking of DNA's modified by plasmid PUC and having a single strand.

There has, therefore, been proposed a process which employs the Sanger method with the PCR method which employs polymerase having a high temperature. DNA is thermally modified into single-strand, or template DNA, and a primer is annealed onto the template DNA. Then, the Sanger method is applied to the template DNA to synthesize thereon a complementary DNA fragment of any length ending with four different kinds of bases. The PCR method is applied to the template DNA on which the complementary DNA fragment has been formed, so that the template DNA may be separated from the complementary DNA fragment. The annealing of the primer onto the template DNA, and the Sanger and PCR methods are repeated several tens of times to produce a large amount of complementary DNA fragments, whereby an improved accuracy of electrophoretic identification can be achieved to determine the sequence of bases in DNA correctly.

In the process which employs the Sanger method in combination with the PCR method, however, the electrophoretic operation is completely separated from the treatment of a sample by the Sanger method. The sample is treated by the Sanger method, and is transferred by a pipette, or the like to a electrophoretic apparatus. As there is no alternative but to do any such work manually, the above process cannot automatically determine the sequence of bases in DNA.

SUMMARY OF THE INVENTION

It is, therefore, an object of this invention to enable the treatment of a sample at a controlled temperature and the electrophoretic treatment thereof to be carried out successively and automatically.

It is another object of this invention to enable the base sequence of DNA to be determined automatically.

According to one aspect of this invention, there is provided an electrophoretic apparatus which comprises a sample introducing section, a temperature control section for controlling the temperature of the sample in the sample introducing section, an electrophoretic section for subjecting the temperature-controlled sample to electrophoresis in a gel for separation into fragments. and a section for analyzing the fragments. The apparatus makes it possible to carry out automatically a series of operations including the treatment of the sample at a controlled temperature and the electrophoretic treatment thereof.

According to another aspect of this invention, there is provided a process for determining the base sequence of DNA which comprises the steps of treating DNA in accordance with the Sanger method to form complementary DNA fragments of different lengths ending specifically with four different kinds of bases; separating the fragments from one another by electrophoresis; and identifying the base at the end of each of the fragments, the step being carried out successively and automatically. It is easier to determine the base sequence of DNA by the process of this invention than by the conventional process in which the step of forming complementary DNA fragments and the step of separating them by electrophoresis are carried out independently of each other.

According to still another aspect of this invention, there is provided an apparatus for determining the base sequence of DNA which comprises a section for introducing a sample of DNA containing the necessary reagent for the Sanger method, a temperature control section for controlling the temperature of the sample in the sample introducing section in accordance with the temperature program of the Sanger method to form complementary DNA fragments of different lengths ending specifically with four different kinds of bases, an electrophoretic section for separating the complementary DNA fragments in the sample introducing section from one another by electrophoresis, and a detecting section for identifying the base at the end of each of the complementary DNA fragments. The apparatus enables the automatic sequencing of bases in DNA by carrying out the treatment of the sample at a controlled temperature and the electrophoretic treatment thereof successively.

These and other objects and advantages of this invention will become more apparent from the following description and the accompanying drawings.

DESCRIPTION OF THE PREFERRED EMBODIMENT

Figure 1:
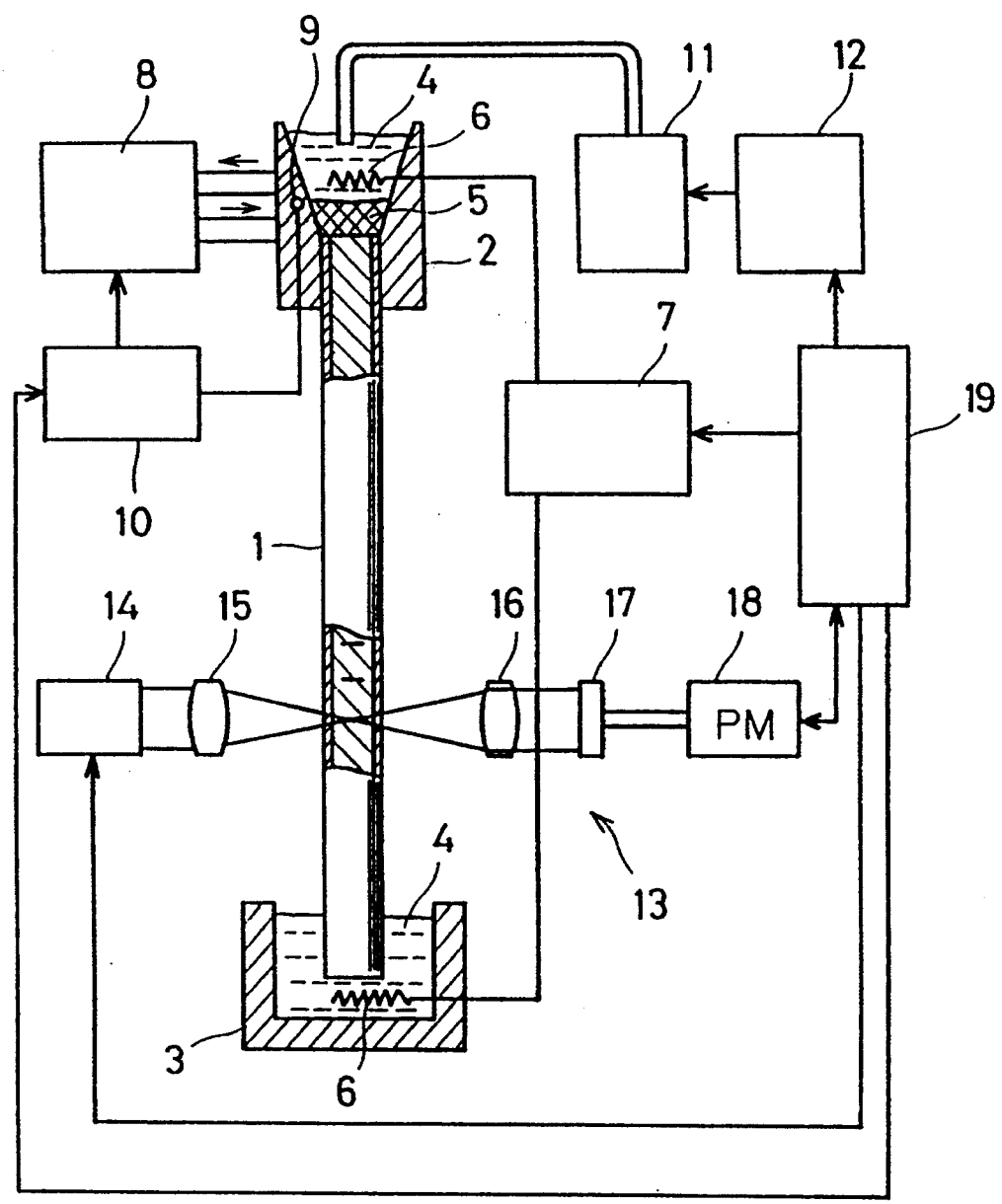
FIG. 1 is a diagrammatic representation of an electrophoretic apparatus embodying this invention.
Figure 2:
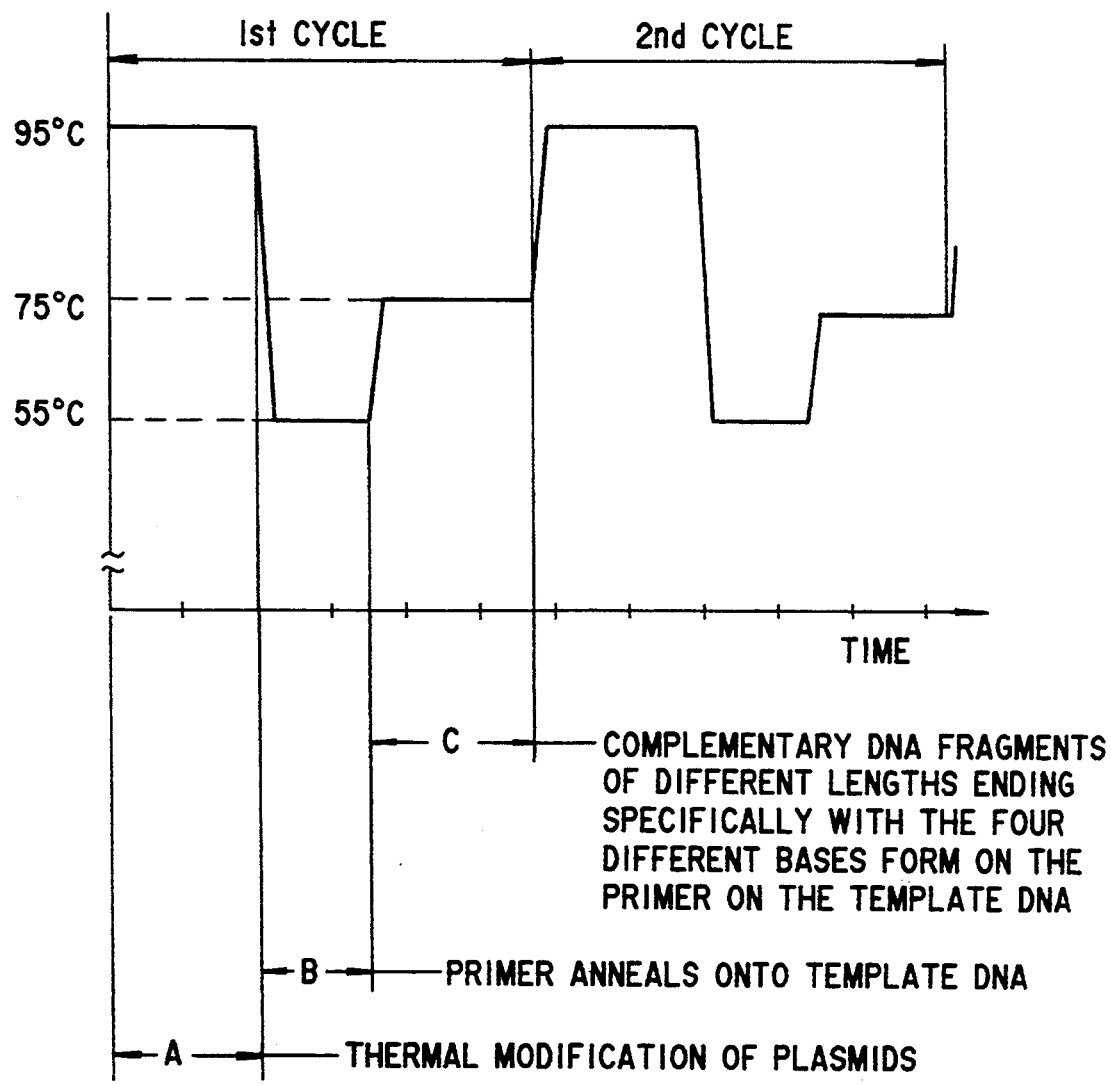
FIG. 2 is a graph showing a temperature cycle employed in the apparatus.

An electrophoretic apparatus embodying this invention is shown in FIG. 1. The apparatus is intended for use in determining the base sequence of DNA in accordance with the Sanger method. The apparatus consists mainly of a sample introducing device 2 and an electrophoretic vessel 3 provided at the top and bottom, respectively, of a glass capillary 1. The capillary 1 holds a polyacrylamide gel. The sample introducing device 2 is adapted for receiving the supply of a sample of DNA, DNA polymerase and a Sanger reagent, as well as an electrolytic buffer solution 4. The electrophoretic vessel 3 is adapted for holding the buffer solution 4. The sample introducing device 2 and the electrophoretic vessel 3 are each provided with an electrode 6 which is connected to a high-voltage power-supply device 7.

A heating and cooling device 8 is connected to the sample introducing device 2 for heating or cooling the mixture of the sample and the reagent therein. The sample introducing device 2 is provided with a temperature sensor 9. The heating and cooling device 8 and the temperature sensor 9 are connected to a temperature controller 10 which controls the heating and cooling device 8 in accordance with the output of the temperature sensor 9.

A device 11 for supplying the buffer solution has a supply pipe 11a terminating in the sample introducing device 2. A device 12 for controlling the supply of the buffer solution is connected to the buffer solution supplying device 11 for controlling it so that it may supply the buffer solution into the sample introducing device 2 upon completion of the treatment of the sample therein.

A fluorescent detecting device 13 is positioned across the middle portion of the glass capillary 1 for detecting the fluorescent pigment combined with the end of each of DNA fragments separated by electrophoresis in the capillary 1. The fluorescent detecting device 13 consists mainly of a laser 14, a converging lens 15 for converging in the capillary 1 light emitted by the laser 14, a lens 16 for diverging into parallel rays the light leaving the capillary 1, an interference filter 17 for detecting the wavelength of the light leaving the lens 16, and a photo-multiplier (PM) 18 for detecting the light leaving the filter 17.

The temperature controller 10, the device 12 for controlling the supply of the buffer solution, the high-voltage power-supply device 7, the laser 14 and the photo-multiplier 18 are connected to a data control analyzer 19 which controls them and determines the base sequence of DNA in accordance with the output of the photomultiplier 18.

Description will now be made of a process in which the electrophoretic apparatus as hereinabove described is used to determine the base sequence of DNA. The sample introducing device 2 is supplied with a mixed solution containing DNA of which the base sequence is to be determined, a primer with which a fluorescent substance, such as FITC, is combined, a Sanger reagent, and DNA polymerase required for the PCR reaction. The heating and cooling device 8 is controlled by the temperature controller 10 to control the temperature of the mixed solution in the sample introducing device 2. More specifically, the solution is maintained at a temperature of 95° C. for about one minute, so that the thermal modification of plasmids may cause the conversion of DNA to single-strand, or template DNA. The solution is cooled to a temperature of 55° C., and maintained at that temperature for about 30 seconds, so that the primer may be annealed onto the template DNA. Then, the solution is heated again to a temperature of about 75° C., and maintained at that temperature for about one to three minutes, so that complementary DNA fragments of different lengths ending specifically with four different kinds of bases may be formed on the primer on the template DNA by the Sanger reaction.

The temperature cycle as hereinabove described is repeated. When the solution is heated to 95° C., and maintained at that temperature for about one minute, the template DNA and the complementary DNA fragments are separated from each other. When the solution is cooled to 55° C., the primer is annealed onto the template DNA again. And when the solution is heated to about 75° C. again, the Sanger reaction takes place again to form complementary DNA fragments on the template DNA. The cycle is repeated, for example, 10 to 30 times until the solution is finally maintained at 70° C. for seven minutes, whereby a large amount of complementary DNA fragments of different lengths are produced.

Upon completion of the repeated cycle, the buffer solution 4 is supplied from the buffer solution supplying device 11 to the sample introducing device 2, and a high voltage is applied across the electrodes 6 by the high-voltage power-supply device 7. The complementary DNA fragments of different lengths in the sample introducing device 2 start electrophoretic movement through the glass capillary 1, and are separated from one another in the polyacrylamide gel, beginning with ones of short length, and resulting in the formation of a DNA band 20, as shown in FIG. 1. Each DNA band 20 emits fluorescent light upon application of laser light, as the complementary DNA fragments forming it contain a fluorescent pigment. Wherein the wavelength of the fluorescent light emitted by each DNA band 20 is determined by the photomultiplier 18, it is possible to identify the base at the end of the complementary DNA fragment forming the DNA band 20. Wherein the bases at the ends of the complementary DNA fragments are determined one after another from the lower DNA bands 20, it is possible to determine the base sequence of DNA.

The electrophoretic apparatus as hereinabove described makes it possible to carry out successively the Sanger treatment of the sample combined with the PCR method and the electrophoretic treatment thereof, and thereby determine the base sequence of DNA automatically.

Although the invention has been described with reference to the electrophoretic apparatus or process employing a capillary gel, it is equally applicable to an apparatus or process employing a slab, or other gel, too. Although the base sequence of DNA has been described as being determined by a fluorescent system, this invention is equally applicable to an apparatus or process employing another detecting system relying upon, for example, a mass spectrum, too.

The invention has been described with reference to a preferred embodiment thereof. It is to be understood that variations or modifications may be easily made by anybody of ordinary skill in the art without departing from the scope of this invention which is defined by the appended claims.

What is claimed is:

1. An electrophoretic apparatus comprising:
   means for introducing a sample;
   means for controlling the temperature of said sample in said sample introducing means;
   electrophoretic means for causing the electrophoresis of said temperature-controlled sample in a gel to separate said sample into fragments; and
   means for analyzing said fragments.

2. An apparatus as set forth in claim 1, wherein said sample introducing means is provided with means for supplying a buffer solution to said sample introducing means.

3. An apparatus as set forth in claim 2, wherein said temperature controlling means comprises a heating and cooling device, a temperature controller for controlling said heating and cooling device, and a temperature sensor positioned in said sample introducing means and connected to said temperature controller.

4. An apparatus as set forth in claim 3, wherein said electrophoretic means comprises a glass capillary filled with said gel, and having one end connected to said sample introducing means, the other end thereof being positioned in an electrophoretic vessel holding a buffer solution, and a pair of electrodes located in said sample introducing means and said vessel, respectively, and connected to a high-voltage power-supply device.

5. An apparatus as set forth in claim 4, wherein said analyzing means comprises a fluorescent detecting device.

6. An apparatus as set forth in claim 5, wherein said fluorescent detecting device comprises a laser, a converging lens for converging light from said laser in said capillary, a lens for diverging said light leaving said capillary into parallel rays, an interference filter for detecting the wavelength of said light leaving said diverging lens, and a photomultiplier for detecting said light leaving said filter.

7. An apparatus as set forth in claim 1, wherein said sample is of DNA and contains a reagent required for the Sanger method.

8. An apparatus as set forth in claim 7, wherein said temperature controlling means is adapted for controlling said temperature so that said sample may be treated in accordance with a temperature program of the Sanger method.

9. An apparatus for determining the base sequence of DNA which comprises:
   means for introducing a sample of DNA containing a reagent required for the Sanger method;
   means for controlling the temperature of said sample in said sample introducing means in accordance with a temperature program of the Sanger method to form complementary DNA fragments of different lengths ending specifically with four different kinds of bases;
   electrophoretic means for causing the electrophoresis of said fragments to separate them from one another, and
   detecting means for identifying the base at the end of each of said separated fragments.

10. An apparatus as set forth in claim 9, wherein said sample introducing means is provided with means for supplying a buffer solution to said sample introducing means.

11. An apparatus as set forth in claim 10, wherein said temperature controlling means comprises a heating and cooling device, a temperature controller for controlling said heating and cooling device, and a temperature sensor positioned in said sample introducing means and connected to said temperature controller.

12. An apparatus as set forth in claim 11, wherein said electrophoretic means comprises a glass capillary filled with a gel, and having one end connected to said sample introducing means, the other end thereof being located in an electrophoretic vessel holding a buffer solution, and a pair of electrodes located in said sample introducing means and said vessel, respectively, and connected to a high-voltage power-supply device.

13. An apparatus as set forth in claim 12, wherein said detecting means comprises a fluorescent detecting device.

14. An apparatus as set forth in claim 13, wherein said fluorescent detecting device comprises a laser, a converging lens for converging light from said laser in said capillary, a lens for diverging the light leaving said capillary into parallel rays, an interference filter for detecting the wavelength of the light leaving said diverging lens, a photomultiplier for detecting the light leaving said filter, and a data analyzing for determining the base sequence of said DNA in accordance with the output of said photomultiplier.

* * * * *